(12) United States Patent
Breitbart et al.

(10) Patent No.: US 6,398,816 B1
(45) Date of Patent: Jun. 4, 2002

(54) GENETIC ENGINEERING OF CELLS TO ENHANCE HEALING AND TISSUE REGENERATION

(75) Inventors: Arnold S. Breitbart, Great Neck; Daniel A. Grande, Sea Cliff; James M. Mason, Bethpage, all of NY (US)

(73) Assignee: North Shore-Long Island Jewish Research Institute, Manhasset, NY (US)

( * ) Notice: Subject to any disclaimer, the term of this patent is extended or adjusted under 35 U.S.C. 154(b) by 0 days.

(21) Appl. No.: 09/489,756

(22) Filed: Jan. 21, 2000

Related U.S. Application Data

(63) Continuation of application No. 08/923,718, filed on Sep. 4, 1997, now Pat. No. 6,077,987.

(51) Int. Cl.$^7$ .................................................. A61F 2/36
(52) U.S. Cl. ...................... 623/23.72; 424/422; 424/423
(58) Field of Search .............................. 623/11, 16, 18, 623/66; 435/172.1, 172.3, 69.1, 375, 377; 424/422, 423

(56) References Cited

U.S. PATENT DOCUMENTS

| 1,995,970 A | 3/1935 | Dorough |
| 2,676,945 A | 4/1954 | Higgins |
| 2,683,136 A | 7/1954 | Higgins |

(List continued on next page.)

FOREIGN PATENT DOCUMENTS

| WO | WO 95/11983 | 5/1995 |
| WO | WO 97/14783 | 4/1997 |
| WO | WO 97/30662 | 8/1997 |

OTHER PUBLICATIONS

Ahrens, et al, "Expression of human bone morphogenic proteins –2 or –4 in murine mesenchymal progenitor C3H10T1 ½cells induces differentiation into distinct mesenchymal cell lineages," *DNA and Cell Biology* 12(10): 871–880 (1993).

Allcock, et al., "Synthesis and Hydrolysis of Hexakis(imidazolyl)cyclotriphosphazene," *J. Am. Chem. Soc.* 103:2250–2256 (1981).

Beresfor, et al., "Further Characterisation of a System for the Culture of Human Bone Cells," *Calcif. Tissue Int.* 35(⅘):637 (Abstract only) (1983).

Cheung, et al., "Growth of osteoblasts on porous calcium phosphate ceramic: an in vitro model for biocompatability study," *Biomaterials* 10:63–67 (1989).

Choy, et al., "Fibroblast Behavior in the Embryonic Chick Heart," *Dev. Dyn.* 198(2):97–107 (1993).

Chu, "Survey of Clinically Important Wound Closure Biomaterials," *Biocompatible Polymers, Metals and Composites*, (Szycher, ed.), p. 477 (Technomic Publishing Lakewood, NJ 1983).

Cohn, et al., "Isolated Bone Cells," in *Skeletal Research: An Experimental Approach* (Simmons, et al., ed.), pp. 3–20 (Academic Press, NY 1979).

Elgendy, et al. "Osteoblast–like cell (MC3T3–E1) proliferation on bioerodible polymers: An approach towards the development of a bone–bioerodible polymer composite material," *Biomaterials* 14(4):263–269 (1993).

Felgner, et al., "LipofectAMINE™ Reagent: A New, Higher Efficiency Polycationic Liposome Transfection Reagent," *Focus/Gibco* 15(3):73–78 (1993).

Frame, "Hydroxyapatite as a biomaterial for alveolar ridge augmentation," *Int. J. Oral Maxillofacial Surgery* 16:642–655 (1987).

Friedlaender, "Current Concepts Review: Bone Grafts," *Journal of Bone and Joint Surgery* 69A(5):786–790 (1987).

Galileo, et al., "Neurons and glia arise from a common progenitor in chicken optic tectum: Demostration with two retroviruses and cell type–specific antibodies," *Proc. Natl. Acad. Sci. USA* 87(1):458–462 (1990).

Gitelman, et al, "Vgr–1/BMP–6 induces osteoblastic differentiation of pluripotential mesenchymal cells," *Cell Growth and Differentiation* 6(7):827–836 (1995).

(List continued on next page.)

*Primary Examiner*—David J. Isabella
*Assistant Examiner*—Urmi Chattopadhyay
(74) *Attorney, Agent, or Firm*—Holland & Knight LLP

(57) ABSTRACT

A method for enhancing and/or increasing the efficiency of repair of tissues, primarily bone or cartilage, using genetically engineered cells has been developed. In the preferred embodiment, mesenchymal stem cells are isolated from periosteum tissue, and transfected with the gene encoding a growth factor for the particular cell type to be repaired. For example, for repair of bone, a gene (or genes) encoding bone morphogenic protein is transfected into periosteal cells. The transfected periosteal cells then express the bone morphogenic protein in culture to promote bone repair as a function of the expressed bone morphogenic protein. Cells can be transfected using any appropriate means, including viral vectors, as shown by the example, chemical transfectants, or physico-mechanical methods such as electroporation and direct diffusion of DNA. Genes can encode any useful protein, for example, a specific growth factor, morphogenesis factor, a structural protein, or a cytokine which enhances the temporal sequence of wound repair, alters the rate of proliferation, increases the metabolic synthesis of extracellular matrix proteins, or directs phenotypic expression in endogenous cell populations. Representative genes encoding proteins include bone growth factor genes, cartilage growth factor genes, nerve growth factor genes, and general growth factors important in wound healing, such as platelet-derived growth factor (PDGF), vascular endothelial growth factor (VEGF), insulin-like growth factor (IGF-1), epidermal growth factor (EGF), basic fibroblast growth factor (FGF), endothelial derived growth supplement.

9 Claims, No Drawings

U.S. PATENT DOCUMENTS

| | | | |
|---|---|---|---|
| 2,703,316 A | | 3/1955 | Schneider |
| 2,758,987 A | | 8/1956 | Salzberg |
| 2,951,828 A | | 9/1960 | Zeile et al. |
| 3,371,069 A | | 2/1968 | Takashi et al. |
| 3,531,561 A | | 9/1970 | Trehu |
| 4,846,835 A | | 7/1989 | Grande |
| 5,041,138 A | | 8/1991 | Vacanti et al. |
| 5,226,914 A | | 7/1993 | Caplan et al. |
| 5,486,359 A | | 1/1996 | Caplan et al. |
| 5,492,697 A | | 2/1996 | Boyan et al. |
| 5,563,124 A | | 10/1996 | Damien et al. |
| 5,591,453 A | | 1/1997 | Ducheyne et al. |
| 5,632,745 A | | 5/1997 | Schwartz |
| 5,693,341 A | * | 12/1997 | Schroeder et al. .......... 424/488 |
| 5,763,416 A | * | 6/1998 | Bonadio et al. .............. 514/44 |

OTHER PUBLICATIONS

Goldberg, et al., "Effect of Gold Sodium Thiomalate on Proliferation of Human Rheumatoid Synovial Cells and on Collagen Synthesis in Tissue Culture," *Biochem. Pharmacol.* 29(6):869–876 (1980).

Gundberg, et al., "Measurements of γ–carboxyglutamate and circulating osteocalcin in normal children and adults," *Clin. Chem. Acta* 128:1–8 (1983).

Hollinger, et al., "Biodegradable Bone Repair Materials," *Clinical Orthopedics and Related Research* 207:290–305 (1986).

Hollinagel, et al, "Parathyroid Hormone (PTH) and PTH/PTHRP–Receptor Mediated Stimulation of Osteochondrogenic Development in BMP–Transfected C3H10T½Mesenchymal Progenitor Cells," *Calcified Tissue International* 56(5): 430 (1995).

Jarcho, "Calcium Phosphate Ceramics as Hard Tissue Prosthetics," *Clinical Orthopaedics and Related Research* 157:259–278 (1981).

Kulkarni, et al., "Biodegradable Poly(lactic acid) Polymers," *J. Biomedical Materials Research* 5:169–181 (1971).

Laurencin, et al. "Use of polyphosphazenes for skeletal tissue regeneration," *J. Biom. Mater. Res.* 27(7):963–973 (1993).

Mason, et al, "Expression of human bone morphogenic protein 7 in primary rabbit periosteal cells: potential utility in gene therapy for osteochondral repair," *Gene Therapy* 5(8):1098–1104 (1998).

Miller, et al., "Improved Retroviral Vectors for Gene Transfer and Expression," *Bio Techniques* 7(9):980–990 (1989).

Miller, et al., "Redesign of Retrovirus Packaging Cell Lines to Avoid Recombination Leading to Helper Virus Production," *Mol. Cel. Biol.* 6(8):2895–2902 (1986).

Nabel, et al., "Direct gene transfer with DNA–liposome complexes in melanoma: Expression, biological activity and lack of toxicity in humans," *Proc. Nat. Acad. Sci. USA* 90(23):11307–11311 (1993).

Neville, "Molecular Weight Determination of Protein–Dodecyl Sulfate Complexes by Gel Electrophoresis in a Discontinous Buffer System," *J. Biol. Chem.* 246(20):6328–6334 (1971).

Owen, "Marrow stromal stem cells," *J. Cell Sci.* (Suppl.) 10:63–76 (1988).

Ozkaynak, et al., "OP–1 cDNA encodes and osteogenic protein in the TGF–β family," *EMBO J.* 9(7):2085–2093 (1990).

Parsons, et al. "Osteoconductive Composite Grouts for Orthopedic Use," *Annals N.Y. Academy of Sciences* 523:190–207 (1988).

Partridge, "Muscle transfection made easy," *Nature* 352(6338):757–758 (1991).

Pate, et al., "Isolation and Differentiation of Mesenchymal Stem Cells from Rabbit Muscle," *Proc. 49th Ann. Sess. Forum Fundamental Surg. Problems* pp. 587–589 (Oct. 10–15, 1993).

Peck, et al., "Bone Cells: Biochemical and Biological Studies after Enzymatic Isolation," *Science* 146:1476–1477 (1964).

Peck, et al., "Cyclic 3'5' Adenosine Monophosphate in Isolated Bone Cells: Response to Low Concentrations of Parathyroid Hormone," *Endocrinology* 92(3):692–697 (1982).

Ritsilä, et al., "Periosteal and Perichondral Grafting in Reconstructive Surgery," *Clin. Orthop. Related Res.* 302:259–265 (1994).

Rogers, et al., "Differentiation Factors Induces Expression of Muscle, Fat, Cartilage, and Bone in a Clone of Mouse Pluripotent Mesenchymal Stem Cells," *Am. Surg.* 61(3):231–236 (1995).

Tuli, et al., "N°–Benzyladenine: Inhibitor of Respiratory Kinases," *Science* 146:1477–1479 (1964).

Wade, et al. "Biocompatibility of eight poly(organophosphazenes)," in *Organomet. Polym.*, pp. 283–288 (Carraher, et al., eds.) (Academic Press, New York, 1978).

Wilson, "Vehicles for gene therapy," *Nature* 365(6448):691–692 (1993).

Wivel, et al., "Germ–Line Gene Modification and Disease Prevention: Some Medical and Ehtical Perspectives," *Science* 262:533–538 (1993).

Wolff, "Human dystrophin expression in mdx mice after intramuscular injection of DNA constructs," *Nature* 352(6338):815–818 (1991).

Wolff, et al., "Direct Gene Transfer into Mouse Muscle in Vivo," *Science* 247:1465–1468 (1990).

Woo, et al., "In Vivo Gene Therapy of Hemophilia B: Sustained Partial Correction in Factor IX–Deficient Dogs," *Science* 262:117–119 (1993).

Yaszemski, et al., "Evolution of bone transplantation: molecular, cellular and tissue strategies to engineer human bone," *Biomaterials* 17:175–85 (1996).

Young, et al., "Pluripotent mesenchymal stem cells reside within avian connective tissue matrices," *In Vitro Cell. Dev. Biol. Anim.* 29A(9):723–736 (1993).

* cited by examiner

GENETIC ENGINEERING OF CELLS TO ENHANCE HEALING AND TISSUE REGENERATION

This application is a continuation of U.S. application Ser. No. 08/923,718 filed Sep. 4, 1997, now U.S. Pat. No. 6,077,987.

BACKGROUND OF THE INVENTION

The present invention is generally in the area of methods for repair and reconstruction of bone, cartilage and enhancement of healing of other tissues.

Bone is built of a dense network of collagen protein fibers arranged in layers with crystals of calcium phosphate and calcium carbonate between the fibers. About 25% of the bone's weight is calcium. About four percent of the bone's volume, scattered evenly throughout it, are living cells called osteocytes. These are supplied with oxygen and nutrients through a network of very small blood vessels that extend throughout the bone. Defects in the bone are repaired by osteoclasts removing the damaged bone, then osteoblast cells laying down new bone. The osteoblasts repeatedly form layers, each consisting of a network of collagen fibers, which produce enzymes resulting in calcium and phosphorus deposition, until the defect is repaired.

Bone repair has been primarily achieved using bone cements, pins, screws and other devices for mechanical stabilization. Larger defects, however, arising from trauma or surgery, require replacement of the missing bone with a material that provides support and which can be immobilized, yet which is also biocompatible. A graft may be necessary when bone fails and does not repair itself in the normal amount of time or when bone loss occurs through fracture or tumor. Bone grafts must serve a dual function: to provide mechanical stability and to be a source of osteogenesis. Since skeletal injuries are repaired by the regeneration of bone rather than by the formation of scar tissue, grafting is a viable means of promoting healing of osseous defects, as reviewed by Friedlaender, G. E., "Current Concepts Review: Bone Grafts," Journal of Bone and Joint Surgery, 69A(5), 786–790 (1987). Osteoinduction and osteoconduction are two mechanisms by which a graft may stimulate the growth of new bone. In the former case, inductive signals of little-understood nature lead to the phenotypic conversion of connective tissue cells to bone cells. In the latter, the implant provides a scaffold for bony ingrowth. The bone remodeling cycle is a continuous event involving the resorption of pre-existing bone by osteoclasts and the formation of new bone by the work of osteoblasts. Normally, these two phases are synchronous and bone mass remains constant. However, the processes become uncoupled when bone defects heal and grafts are incorporated. Osteoclasts resorb the graft, a process which may take months. More porous grafts revascularize more quickly and graft resorption is more complete. After the graft has been resorbed, bone formation begins. Bone mass and mechanical strength return to near normal.

Present methods for the repair of bony defects include grafts of organic and synthetic construction. Three types of organic grafts are commonly used: autografts, allografts, and xenografts. An autograft is tissue transplanted from one site to another in the patient. The benefits of using the patient's tissue are that the graft will not evoke a strong immune response and that the material may or may not be vascularized, which allows for speedy incorporation. However, using an autograft requires a second surgery, which increases the risk of infection and introduces additional weakness at the harvest site. Further, bone available for grafting may be removed from a limited number of sites, for example, the fibula, ribs and iliac crest. An allograft is tissue taken from a different organism of the same species, and a xenograft from an organism of a different species. The latter types of tissue are readily available in larger quantities than autografts, but genetic differences between the donor and recipient may lead to rejection of the graft. Periosteal and perichonchondral grafting has also been attempted, as described by Ritsitä, et al., Clin. Orthop. Related Res. 302, 259–265 (1994). Examples of synthetic materials which have been used include titanium and steel alloys, particularly those having a porous structure to allow ingrowth of cells to stabilize the implant, bone cements, alone or mixed with cells, sterilized bone, and polymeric or polymeric/hydroxyapatite implants. Bioerodible polymers have been used in people for thousands of years, with plain gut (collagen) sutures being used since 175 A.D.(12), as reported by Chu, In Biocompatible Polymers, Metals and Composites, ed. Szycher, M, p. 477 (Technomic Publishing Lakewood, N.J. 1983). The first synthetic biodegradable biopolymers, polylactic acid and polyglycolic acid, were suggested for in vivo use in U.S. Pat. No. 3,371,069 to Schmidt. All have advantages and disadvantages, yet none provides a perfect replacement for the missing bone.

Large defects are particularly difficult. One approach has been to seed fibrous biodegradable polymeric matrices with bone-forming cells, then overlay the matrix onto the defect. As the cells proliferate, and surrounding tissues grow into the defect, the matrix will degrade, leaving the new tissue. As described in U.S. Pat. No. 4,846,835 to Grande and U.S. Pat. No. 5,041,138 to Vacanti, et al., cartilage has been grown by seeding synthetic polymeric matrices with dissociated cells, which are then implanted to form new cartilage.

The first description of bone cells in culture was by Peck, et al., in Science 146, 1476 (1964). Since that time, many studies have focused on the maintenance of viable cell cultures of osteoblasts with full expression of phenotype, as discussed by Peck, et al., Endocrinology 92, 692 (1982). Other studies examining bone cell growth and activity regulation in vitro have identified various factors necessary for cell development, as reported by Beresfor, et al., Calcif. Tissue Int. 35, 637 (1983). Studies on osteoblast growth on supports outside of the traditional tissue culture environment have concentrated on studying the growth of these cells on mineral matrices which mimic the natural hydroxyapatite environment in vivo, as reported by Chueng and Haak, Biomaterials 10, 63 (1989). Hydroxyapatite (HA), $Ca_3(PO_4)_2.Ca(OH)_2$, is a natural mineral structure that resembles the crystal lattice of bones. Studies on the growth of osteoblasts in culture on calcium phosphate ceramic surfaces demonstrated that osteoblasts, fibroblasts and chondrocytes attach to the ceramic material and form multicellular layers. Retention of phenotypic activity of osteoblasts was demonstrated through parathyroid hormone suppression of alkaline phosphatase activity, and cAMP increase as well as expression of Type I collagen.

The cell source is in some cases determinative of the usefulness of this method. It is clearly most desirable to use a patient's own cells to repair a defect, thereby avoiding problems with immune rejection or contamination. Sources of cells include growing and mature bone, cartilage, and mesenchymal stem cells. Chondro/osteoprogenitor cells, which are bipotent with the ability to differentiate into cartilage or bone, have been isolated from bone marrow (for example, as described by Owen, J. Cell Sci. Suppl. 10, 63–76 (1988) and in U.S. Pat. No. 5,226,914 to Caplan, et al.). These cells led Owen to postulate the existence of pluripotent mesenchymal stem cells, which were subsequently isolated from muscle (Pate, et al., *Proc. 49th Ann. Sess. Forum Fundamental Surg. Problems* 587–589 (Oct. 10–15, 1993)), heart (Dalton, et al., *J. Cell Biol.* 119, R202 (March 1993)), and granulation tissue (Lucas, et al., *J. Cell Biochem.* 122, R212 (March 1993)). Pluripotency is demonstrated using a non-specific inducer, dexamethasone (DMSO), which elicits differentiation of the stem cells into chondrocytes (cartilage), osteoblasts (bone), myotubes (muscle), adipocytes (fat), and connective tissue cells. There remains a need for a ready source of cells for use in repairing bone defects.

Conventional orthopedic and craniofacial bone reconstruction involves the use of autogenous bone which has the disadvantages of limited amount of bone and donor site morbidity, as well as the use of alloplastic materials which have an increased infection rate. Previous work by North Shore University Hospital Research Corporation, described in PCT/US96/16664 entitled "Tissue-Engineered Bone Repair Using Cultured Periosteal Cells", used cultured cells derived from periosteum to repair cartilage and bone defects.

It is an object of the present invention to provide a method and materials for repair of bone and cartilage defects as well as other tissue injuries using cells which have been genetically modified to deliver a specific growth factor, morphogenesis factor, or cytokine in order to enhance the temporal sequence of wound repair.

It is a further object of the present invention to provide a method and cells to produce protein factors having structural as well as metabolic functions.

SUMMARY OF THE INVENTION

A method for enhancing and/or increasing the efficiency of repair of tissues, primarily bone or cartilage, using genetically engineered cells has been developed. In the preferred embodiment, cells are isolated from periosteum tissue, and transfected with the gene encoding a growth factor for the particular cell type to be repaired. For example, for repair of bone, a gene (or genes) encoding bone morphogenic protein is transfected into periosteal cells. The transfected periosteal cells then express the bone morphogenic protein in culture and promote bone repair as a function of the expressed bone morphogenic protein. Cells can be transfected using any appropriate means, including viral vectors, as shown by the example, chemical transfectants, or physico-mechanical methods such as electroporation and direct diffusion of DNA. Genes can encode any useful protein, for example, a specific growth factor, morphogenesis factor, a structural protein, or a cytokine which enhances the temporal sequence of wound repair, alters the rate of proliferation, increases the metabolic synthesis of extracellular matrix proteins, or directs phenotypic expression in endogenous cell populations. Representative genes encoding proteins include bone growth factor genes, cartilage growth factor genes, nerve growth factor genes, and general growth factors important in wound healing, such as platelet-derived growth factor (PDGF), vascular endothelial growth factor (VEGF), insulin-like growth factor (IGF-1), epidermal growth factor (EGF), basic fibroblast growth factor (FGF), endothelial derived growth supplement.

As demonstrated by the example, cells isolated from periosteal tissue were transfected with a gene encoding a bone growth factor, BMP-7. The cells expressed BMP-7 mRNA and BMP-7 protein and produced hydroxyapatite, the essential mineral of bone. The cells were then seeded onto polymer scaffolds for implantation into rabbit cranial bone defects. Retrieved tissue containing seeded cells was stained to show continued expression of BMP-7 up to four weeks post implantation.

DETAILED DESCRIPTION OF THE INVENTION

It has been discovered that cells can be genetically engineered to produce bioactive molecules which act on the cells that are expressing the molecules, or cells adjacent to or in physiological contact with the genetically engineered cells, to alter their growth, differentiation, and/or efficiency of development into new tissue, thereby either promoting wound healing or formation of new tissue. The finding was made empirically, using mesenchymal cells obtained from periosteum, which were then genetically engineered to express bone morphogenic protein ("BMP"). Possible results could have included feedback inhibition of expression, lack of controlled, normal development, or transient expression of only limited benefit. The actual results obtained show that the cells continue to express the BMP after implantation of the genetically engineered cells, and that the BMP is active on the cells. These results are predictive of results obtained with other cell types and bioactive molecules.

I. Cells

The cells that can be manipulated for use in the methods described herein include almost any type of tissue. These are typically normal mammalian cells, preferably of the same species as the ultimate recipient, most preferably of the same origin as the recipient, although the method can be practiced using xenotransplants which have been altered to decrease the liklihood of rejection, for example, by expression of a complement inhibitor such as CD59, or masking of sugar residues. These techniques are known to those skilled in the art, and have been commercially developed using pigs as the donors, by Alexion Pharmaceuticals, CT, and DNX, PA.

Cell type will typically be selected based on the tissue to be repaired or formed. For example, chondrocytes or fibroblasts can be selected to form cartilage; muscle cells to form muscle. Undifferentiated, or less differentiated, cells may be preferred in some situation. Representative of these cell types include stem cells and mesenchymal cells. In a preferred embodiment, mesenchymal cells are obtained from periosteum, then genetically engineered. Specific examples of cells that can be used to aid healing, repair or formation of bone include osteocytes/osteoblasts and periosteal cells, particularly in combination with BMP- 2–15 and/or IGF. Specific examples of cells that can aid healing, repair or formation of cartilage include chondrocytes and periosteal cells, particularly in combination with CGF and/or TGF-beta. Specific examples of cells that can aid healing, repair or formation of skin include dermal and epidermal cells, particularly in combination with PDGF, VEGF, IGF, and GH. Specific examples of cells that can aid healing, repair or formation of nervous tissue include nerve cells and support cells, particularly in combination with NGF. In most cases, cells will be obtained from a tissue biopsy, which is digested with collagenase or trypsin to dissociate the cells. Alternatively, cells can be obtained from established cell lines or from embryonic cell sources.

Periosteum is a dense, white, fibrous covering around the surface of the bone not covered by articular cartilage. The periosteum consists of two layers. The outer fibrous layer is composed of connective tissue containing blood vessels, lymphatic vessels, and nerves that pass into the bone. The inner osteogenic layer contains elastic fibers, blood vessels, and osteoprogenitor cells and osteoblasts. The periosteum is essential for bone growth, repair and nutrition. It also serves as a point of attachment for ligaments and tendons.

Periosteum consists of multipotent mesodermal cells. Periosteum has the capacity to form all varieties of connective tissue. The advantage of the procedure is that it does not require removal of bone per se. Periosteum is obtained by surgically removing the periosteum from bone. The periosteum is dissected carefully using sharp periosteal elevators. Care is taken to ensure the cambium layer is removed completely. Confirmation of harvest can be accomplished by frozen or conventional histology.

The periosteum is digested using collagenase and trypsin as described by Cohn and Wong, In *Skeletal Research* ed. Simmons and Kunin, p. 3 (Academic Press, N.Y. 1979). Alternatively, cell lines can be established by explant culture. Cells are cultured in Ham's F-12 medium (Gibco) at pH 7.6 supplemented with penicillin (100 U/cc), streptomycin sulfate (100 $\mu$g/cc), magnesium sulfate (200 $\mu$g/cc), glutamine (58.5 $\mu$g/cc) and fetal bovine serum at a final concentration of 12%. Culture medium is replaced three times per week. Cell passage is carried out by incubating monolayers for between five and ten minutes in calcium and magnesium-free Tyrode's solution containing 0.25% trypsin and replating the cells in fresh medium at one-third their confluent density.

Several techniques and materials, alone or in combination, can be employed to promote the osteoblastic phenotype of the periosteal cells, including high oxygen tension, addition of specific compounds or peptides, or specific matrices. In addition to specific matrix interactions, factors determining in vitro differentiation of the cells into bone include high oxygen tension, presence of steroid compounds, especially glucocorticoids such as dexamethasone and other steroidal antiinflammatories and cortisol, proteins and peptides such as calciferol and other enzymes enhancing calcification, beta-glycerolphosphate and other enzymes enhancing phosphorus deposition, prostaglandins such as prostaglandin E2, vitamins C and D and oxygen content. Effective concentrations of the foregoing depend on whether the compounds are used alone or in combination, as well as the relative amounts. Representative concentrations include 0.1 $\mu$M dexamethasone, 40 ng calciferol/ml culture media, 0.1 $\mu$M cortisol, and 0.1 $\mu$M prostaglandin E2.

Agents which enhance differentiation into cartilage are known, for example, transforming growth factor beta 1 at concentrations up to 100 ng/ml. In vivo, even if initially induced in vitro to differentiate into bone, the substrate or site of implantation is the primary factor determining differentiation of the cells into bone.

Cells are examined and characterized by both phase contrast microscopy and light reflectance microscopy. Determination of osteoblast-like character is performed through a variety of methods. Osteocalcin production is measured using the method of Gundberg, Lian, and Gallop, *Clin. Chem. Acta* 128, 1 (1983). Monolayer cultures are washed and incubated in serum-free medium containing 10 mg/cc bovine serum albumin in the absence or presence of 10 nM 1,25(dihydroxy)vitaminD$_3$ for 48 hours. The medium is analyzed by radioinmmunoassay for osteocalcin at the end of the incubation period.

A number of assays can be used to evaluate the cells. For example, cAMP response to parathyroid hormone (PTH) is measured by incubated cultures near confluency with 1 mM isobutylmethylxanthine alone or in combination with 0.2 to 200 ng/cc of PTH with 1–10 ng/cc calcitonin for 10 minutes at 37° C. Incubations are halted by quickly transferring the cultures to ice, washing rapidly with ice-cold Tyrode's solution, and then adding ice-cold ethanol containing 2 mM HCL. After homogenizing the cells in ethanol for 5 seconds, the samples are dried at 100° C. and cAMP concentrations are measured by radioimmunoassay.

Alkaline phosphatase activity of the cell lysates is determined in a similar manner using the method of Luben, Wong and Cohn, *Endocrinology*35, 778 (1983) with n-nitrophenylphosphate as substrate. Collagen synthesis is analyzed according to Schwartz. Cultures are incubated for 48 hours in Minimal Essential Medium (Gibco) containing fetal bovine serum (10%), sodium ascorbate (50 microgram/ml), B-aminopropionitrile and tritiated proline (50 UCi/cc). Collagen from the culture medium and cell layer is isolated, treated with pepsin, and after the addition of carrier type I collagen, analyzed by SDS-PAGE under reducing and non-reducing conditions, as described by Neville, *J. Biol. Chem.* 246, 6326 (1971). Bands of carrier protein are identified by staining with Coomassie blue. The gels are then sliced into 25 equal segments each of which is monitored for radioactive content. Collagen distribution is calculated according to the method of Goldberg, et al., *Biochem. Pharmacol.* 29, 869 (1980).

II. Bioactive Molecules

Genes can encode any useful protein, for example, a specific growth factor, morphogenesis factor, structural protein, or cytokine which enhances the temporal sequence of wound repair, alters the rate of proliferation, increases the metabolic synthesis of extracellular matrix proteins, or directs phenotypic expression in endogenous cell populations. Representative genes encoding proteins include bone growth factor genes (BMPs, IGF) for bone healing, cartilage growth factor genes (CGF, TGF-beta) for cartilage healing, nerve growth factor genes (NGF) for nerve healing, and general growth factors important in wound healing, such as platelet-derived growth factor (PDGF), vascular endothelial growth factor (VEGF), insulin-like growth factor (IGF-1), keratinocyte growth factor (KGF), endothelial derived growth supplement (EDGF), epidermal growth factor (EGF), basic fibroblast growth factor (FGF) for wound and skin healing. Other genes that can be transfected into the cells include genes encoding a protein having a structural function, genes encoding chimeric or fusion proteins, and genes having a general systemic metabolic function, such as factor VIII. The encoded proteins will typically be proteins not normally expressed in the cells, although they can also be proteins which are expressed but in different quantities, with different activities, or under the control of different feedback mechanisms controlling expression.

It is well established that certain bioactive molecules can induce formation of bone or connective tissue. Members of the TGF-beta superfamily appear to play a central role in mesenchymal differentiation, including cartilage and bone formation. TGF-beta enhances bone cell proliferation. The TGF-beta superfamily includes the bone morphogenic proteins, including BMP-2–15 and Insulin-like growth factor (IGF). These can be further divided into three distinct subfamilies: BMP-2, BMP-3, and BMP-7. The different isoforms have different activities in bone morphogenesis and repair. They are closely related to factors which are involved in a variety of developmental processes during embryogenesis. For example, any of BMP 2–7 can be used to induce bone formation and differentiation. IGF has been shown to increase bone formation, promoting fracture healing and inducing bone growth around implants, in conjunction with TGF-beta and BMPs. Other osteoinductive factors such as osteogenin (BMP-3), a skeletal growth factor (SGF), and osteoblast-derived (BDGFs) have also been recently discovered. Other factors shown to act on cells forming bone, cartilage or other connective tissue include retinoids, fibroblast growth factors (FGFs), growth hormone (GH), and transferrin. Proteins specific for cartilage repair include cartilage growth factor (CGF) and TGF-beta. The local microenvironment also affects differentiation and development of cells.

Preferred examples for bone repair and/or treatment of osteoporosis uses periosteal or other mesenchymal stem cells or osteocytes/osteoblasts transfected with bone growth factor genes such as bone morphogenetic protein (BMP) family genes, including BMP 2–15; for cartilage repair uses periosteal cells or chondrocytes transfected with cartilage growth factor genes such as transforming growth factor$\beta$ (TGF-$\beta$) and cartilage growth factor (CGF); for wound healing uses dermal or epidermal cells transfected with growth factor genes such as platelet derived growth factor (PDGF), epidermal growth factor (EGF), vascular endothelial growth factor (VEGF), keratinocyte growth factor (KGF), fibroblast growth factor (FGF), endothelial derived growth supplement (EDGS), or insulin-like growth factor (IGF); for nerve repair (central and/or peripheral) uses neural cells and neural support cells transfected with nerve growth factor (NGF) gene.

III. Means for Genetic Engineering of Cells

Cells can be transfected using any appropriate means, including viral vectors, as shown by the example, chemical transfectants, or physico-mechanical methods such as electroporation and direct diffusion of DNA. See, for example, Wolff, Jon Aal, et, "Direct gene transfer into mouse muscle in vivo," *Science*, 247, 1465–1468, 1990; and Wolff, Jon A, "Human dystrophin expression in mdx mice after intramuscular injection of DNA constructs," *Nature*, 352, 815–818, 1991. Plasmid DNA, which can function episomally, has been used with liposome encapsulation, $CaPO_4$ precipitation and electroporation as an alternative to viral transfections. Clinical trials with liposome encapsulated DNA in treating melanoma is reported by Nabel, J. G., et al., "Direct gene transfer with DNA-liposome complexes in melanoma: Expression, biological activity and lack of toxicity in humans", *Proc. Nat. Acad. Sci. U.S.A.*, 90 (1993) 11307–11311. Felgner, Philip L, "Lipofectamine reagent: A new, higher efficiency polycationic liposome transfection reagent," *Focus/Gibco*, 15, 73–78, 1993; Partridge, Terence A, "Muscle transfection made easy," *Nature*, 352, 757–758, 1991; Wilson, James M, "Vehicles for gene therapy," *Nature*, 365, 691–692, 1993; Wivel, et al., "Germ-line gene modification and disease prevention: Some medical and ethical perspectives," *Science*, 262, 533–538, 1993; and Woo, Savio L Cal, et, "In vivo gene therapy of hemophilia B: sustained partial correction in Factor IX-deficient dogs," *Science*, 262, 117–119, 1993.

As used herein, vectors are agents that transport the gene into the cell without degradation and include a promoter yielding expression of the gene in the cells into which it is delivered. Promoters can be general promoters, yielding expression in a variety of mammalian cells, or cell specific, or even nuclear versus cytoplasmic specific. These are known to those skilled in the art and can be constructed using standard molecular biology protocols. Vectors have been divided into two classes:

a) Biological agents derived from viral, bacterial or other sources.

b) Chemical/physical methods that increase the potential for gene uptake, directly introduce the gene into the nucleus or target the gene to a cell receptor.

Biological Vectors

Viral vectors have higher transaction (ability to introduce genes) abilities than do most chemical or physical methods to introduce genes into cells.

Retroviral vectors are the vectors most commonly used in clinical trials, since they carry a larger genetic payload than other viral vectors. However, they are not useful in non-proliferating cells. Adenovirus vectors are relatively stable and easy to work with, have high titers, and can be delivered in aerosol formulation. Pox viral vectors are large and have several sites for inserting genes, they are thermostable and can be stored at room temperature.

Plasmids are not integrated into the genome and the vast majority of them are present only from a few weeks to several months, so they are typically very safe. However, they have lower expression levels than retroviruses and since cells have the ability to identify and eventually shut down foreign gene expression, the continuous release of DNA from the polymer to the target cells substantially increases the duration of functional expression while maintaining the benefit of the safety associated with non-viral transfections.

Chemical/physical vectors

Other methods to directly introduce genes into cells or exploit receptors on the surface of cells include the use of liposomes and lipids, ligands for specific cell surface receptors, cell receptors, and calcium phosphate and other chemical mediators, microinjections directly to single cells, electroporation and homologous recombination. Liposomes are commercially available from Gibco BRL, for example, as LIPOFECTIN® and LIPOFECTACE®, which are formed of cationic lipids such as N-[1-(2,3 dioleyloxy)-propyl]-n,n,n-trimethylammonium chloride (DOTMA) and dimethyl dioctadecylammonium bromide (DDAB). Numerous methods are also published for making liposomes, known to those skilled in the art.

IV. Implantation

Cells can be implanted directly into a defect in an amount effective to promote repair. Alternatively, the cells are seeded onto and into a matrix for implantation to repair the defect. The cells may be cultured on the matrix in vitro prior to implantation, or implanted immediately upon seeding.

In the preferred embodiment, the matrix is formed of a synthetic, biocompatible polymer, most preferably a biodegradable polymer, more preferably degrading by hydrolysis rather than enzymolysis. In other embodiments, the matrix is formed of a material such as hydroxyapatite or mixtures of hydroxyapatite and polymer, or tricalcium phosphate. Matrix can also be sterilized bone or a porous metal alloy. The matrix can be in the form of a fibrous or sponge like structure, or a hydrogel. The advantage of the biodegradable material is that the only material ultimately remaining in the patient is the bone. The term "bioerodible", or "biodegradable", as used herein refers to materials which are enzymatically or chemically degraded in vivo into simpler chemical species. These materials are well suited to implantation as they can serve as a temporary scaffold to be replaced by host tissue, degrade by hydrolysis to non-toxic products, and be excreted, as described by Kulkarni, et al., *J. Biomedical Materials Research*, 5, 169–81 (1971); Hollinger, J. O. and G. C. Battistone, "Biodegradable Bone Repair Materials," *Clinical Orthopedics and Related Research*, 207, 290–305 (1986).

Either natural or synthetic polymers can be used to form the matrix, although synthetic polymers are preferred for reproducibility and controlled release kinetics. Synthetic polymers that can be used include biocrodible polymers such as poly(lactide) (PLA), poly(glycolic acid) (PGA), poly(lactide-co-glycolide) (PLGA), and other poly(alpha-hydroxy acids), poly(caprolactone), polycarbonates, polyamides, polyanhydrides, polyamino acids, polyortho esters, polyacetals, polycyanoacrylates and degradable polyurethanes, and non-erodible polymers such as polyacrylates, ethylene-vinyl acetate polymers and other acyl substituted cellulose acetates and derivatives thereof, non-erodible polyurethanes, polystyrenes, polyvinyl chloride, polyvinyl fluoride, poly(vinyl imidazole), chlorosulphonated polyolifins, polyethylene oxide, polyvinyl alcohol, and nylon. Although non-degradable materials can be used to form the matrix or a portion of the matrix, they are not preferred. Examples of natural polymers include proteins such as albumin, collagen, synthetic polyamino acids, and prolamines, and polysaccharides such as alginate, heparin, and other naturally occurring biodegradable polymers of sugar units.

Four polymers widely used in medical applications are poly(paradioxanone) (PDS), poly(lactic acid) (PLA), poly (glycolic acid) (PGA), and PLAGA copolymers. Copolymerization enables modulation of the degradation time of the material. By changing the ratios of crystalline to amorphous polymers during polymerization, properties of the resulting material can be altered to suit the needs of the application. These polymers, including poly(lactide-co-glycolic) acid (PLGA), have been used as polymer composites for bone replacement as reported by H. M. Elgendy, et al. "Osteoblast-like cell (MC3T3-E1) proliferation on bioerodible polymers: An approach towards the development of a bone-bioerodible polymer composite material," *Biomaterials*, 14, 263–269 (1993). Substituted polyphosphazenes have been shown to support osteogenic cell growth, as reported by C. T. Laurencin, et al. "Use of polyphosphazenes for skeletal tissue regeneration," *J. Biom. Mater. Res.*, 27 (1993). Poly(organophosphazenes) are high molecular weight polymers containing a backbone of alternating phosphorus and nitrogen atoms. There are a wide variety of polyphosphazenes, each derived from the same precursor polymer, poly(dichlorophosphazene). The chlorine-substituted species can be modified by replacement of the chlorine atoms by different organic nucleophiles such as o-methylphenoxide along with amino acids. The physical and chemical properties of the polymer can be altered by adding various ratios of hydrolytic sensitive side chains such as ethyl glycinate, as described by C. W. R. Wade, et al. "Biocompatibility of eight poly(organophosphazenes)," in *Organomet. Polym.*, C. E. Carraher, J. E. Sheats and C. U. Pitman, Jr., Eds., Academic Press, New York, 1978, pp. 283–288; and H. R. Allcock and T. J. Fuller, "Synthesis and Hydrolysis of Hexakis(imidazolyl)cyclotriphosphazene," *J. Am. Chem. Soc.*, 103, 2250–2256 (1981). This will affect the degradation of the polymer as an implantable and biodegradable material as well as vary the support of osteogenic cells for bone and tissue implants, as shown by Laruencin, et al. (1993).

PLA, PGA and PLA/PGA copolymers are particularly useful for forming the biodegradable matrices. PLA polymers are usually prepared from the cyclic esters of lactic acids. Both L(+) and D(−) forms of lactic acid can be used to prepare the PLA polymers, as well as the optically inactive DL-lactic acid mixture of D(−) and L(+) lactic acids. Methods of preparing polylactides are well documented in the patent literature. The following U.S. Patents, the teachings of which are hereby incorporated by reference, describe in detail suitable polylactides, their properties and their preparation: U.S. Pat. No. 1,995,970 to Dorough; U.S. Pat. No. 2,703,316 to Schneider; U.S. Pat. No. 2,758,987 to Salzberg; U.S. Pat. No. 2,951,828 to Zeile; U.S. Pat. No. 2,676,945 to Higgins; and U.S. Pat. Nos. 2,683,136; 3,531,561 to Trehu. PGA is the homopolymer of glycolic acid (hydroxyacetic acid). In the conversion of glycolic acid to poly(glycolic acid), glycolic acid is initially reacted with itself to form the cyclic ester glycolide, which in the presence of heat and a catalyst is converted to a high molecular weight linear-chain polymer. PGA polymers and their properties are described in more detail in Cyanamid Research Develops World's First Synthetic Absorbable Suture", *Chemistry and Industry*, 905 (1970).

The erosion of the matrix is related to the molecular weights of PLA, PGA or PLA/PGA. The higher molecular weights, weight average molecular weights of 90,000 or higher, result in polymer matrices which retain their structural integrity for longer periods of time; while lower molecular weights, weight average molecular weights of 30,000 or less, result in both slower release and shorter matrix lives. Poly(lactide-co-glycolide) (50:50), degrades in about six weeks following implantation.

All polymers for use in the matrix must meet the mechanical and biochemical parameters necessary to provide adequate support for the cells with subsequent growth and proliferation. The polymers can be characterized with respect to mechanical properties such as tensile strength using an Instron tester, for polymer molecular weight by gel permeation chromatography (GPC), glass transition temperature by differential scanning calorimetry (DSC) and bond structure by infrared (IR) spectroscopy, with respect to toxicology by initial screening tests involving Ames assays and in vitro teratogenicity assays, and implantation studies in animals for immunogenicity, inflammation, release and degradation studies.

These polymers are particularly useful in forming fibrous or sponge type matrices for implantation. Polymers can also be used to form hydrogels in which the cells are suspended and then implanted.

Another class of materials for making the matrix is hydroxyapatite, or a similar ceramic formed of tricalcium phosphate (TCP) or calcium phosphate (CaPO$_4$). Calcium hydroxyapatites occur naturally as geological deposits and in normal biological tissues, principally bone, cartilage, enamel, dentin, and cementum of vertebrates and in many sites of pathological calcifications such as blood vessels and skin. Synthetic calcium hydroxyapatite is formed in the laboratory either as pure Ca$_{10}$(PO$_4$)$_6$(OH)$_2$ or hydroxyapatite that is impure, containing other ions such as carbonate, fluoride, chloride for example, or crystals deficient in calcium or crystals in which calcium is partly or completely replaced by other ions such as barium, strontium and lead. Essentially none of the geological and biological apatites are "pure" hydroxyapatite since they contain a variety of other ions and cations and may have different ratios of calcium to phosphorous than the pure synthetic apatites.

The synthetic materials are highly diverse, as reported in the literature. As used herein, all of these materials are generally referred to as "hydroxyapatite". Calcium phosphate ceramics can be used as implants in the repair of bone defects because these materials are non-toxic, non-immunogenic, and are composed of calcium and phosphate ions, the main constituents of bone (Jarcho, 1981; Frame, J. W., "Hydroxyapatite as a biomaterial for alveolar ridge augmentation," *Int. J. Oral Maxillofacial Surgery*, 16, 642–55 (1987); Parsons, et al."Osteoconductive Composite Grouts for Orthopedic Use," *Annals N.Y. Academy of Sciences*, 523, 190–207 (1988)). Both tricalcium phosphate (TCP) [$Ca_3(PO_4)_2$] and hydroxyapatite (HA) [$Ca_{10}(PO_4)_6$ $(OH_2)$] have been widely used. Calcium phosphate implants are osteoconductive, and have the apparent ability to become directly bonded to bone. As a result, a strong bone-implant interface is created.

Calcium phosphate ceramics have a degree of bioresorbability which is governed by their chemistry and material structure. High density HA and TCP implants exhibit little resorption, while porous ones are more easily broken down by dissolution in body fluids and resorbed by phagocytosis. However, TCP degrades more quickly than HA structures of the same porosity in vitro. HA is relatively insoluble in aqueous environments. However, the mechanical properties of calcium phosphate ceramics make them ill-suited to serve as a structural element under load bearing circumstances. Ceramics are not preferred since they are brittle and have low resistance to impact loading.

Cells are tested for expression of the transfected gene prior to or days to weeks later following implantation. Expression will typically be required to continue for one to two months for an effect on wound healing.

The present invention will be further understood by reference to the following non-limiting examples.

EXAMPLE 1

Gene Modification of Rabbit Periosteal Cells with Human BMP-7 and Nuclear-localized Betagalactosidase Genes Materials and Methods Cell lines Primary rabbit periosteal cells were obtained from New Zealand white rabbits (Male, 4.5 kg or larger) and cultured in D10 media (high glucose DMEM (Gibco) supplemented with 10% heat-inactivated fetal bovine serum (Hyclone), and 2 mM glutamine). PA317 cells (Miller, A. D. & Buttimore, C. (1986) *Mol. Cel. Biol.* 6, 2895–2902) were the base packaging cell line used to produce retroviral vector particles. 293 cells were the source of RNA used for cloning of the human bone morphogenic protein 7 (hBMP-7) cDNA (Ozkaynak, E. Rueger, D. C., Drier, E. A., Corbett, C., Ridge, R. J., Sampath, T. K., and Oppermann, H. (1990) *EMBO J.* 9, 2085–2093). *Plasmid DNAs, Oligonucleotide Primers, and RT-PCR*

Oligonucleotide primers NS 30 and NS 32 were used according to manufacturers instructions in RT-PCR (Reverse Transcription System Promega) to generate an approximately 1.4 kb cDNA fragment of the hBMP-7 gene from RNA isolated from 293 cells using the RNeasy Total RNA kit (Qiagen). The sequences of the oligonucleotide primers follow:

NS 30: 5' GCGCGTAGAGCCGGCGCGATGCACGT-GCGCTC 3' (SEQ ID NO: 1)

NS 32: 5' CTAGTGGCAGCCACAGGCCCGGACCAC-CATGT 3' (SEQ ID NO: 2)

The approximately 1.4 kb PCR product was cloned into plasmid pT7Blue (Novagen) as per manufacturer's instructions. *E. coli* strain HB101 was generally used in transformations.

Plasmid pT7Blue-hBMP-7#15 was sequenced to verify that the hBMP-7 gene was correct and complete. It was then double digested with HindIII and SmaI and the approximately 1377 bp fragment containing hBMP-7 was isolated. The LNCX-hBMP-7 retroviral vector plasmid was constructed by double digesting plasmid LNCX (Miller, A. D. & Rosman, G. J. (1989) *BioTechniques* 7, 980–990) with HindIII and HpaI and cloning into this site the approximately 1377 bp HindIII/SmaI hBMP-7 fragment.

The LNBeta-actin-hBMP-7 retroviral vector plasmid in which the rat beta-actin promoter/enhancer replaces the CMV promoter/enhancer was constructed by digesting LNCX-hBMP-7 with NruI, Klenow filling the ends, and digesting with HindIII to remove the fragment containing the CMV promoter/enhancer sequence. The approximately 7005 bp NruI/HindIII fragment without CMV was isolated. The rat beta-actin promoter/enhancer was obtained from plasmid pJ6Omega (ATCC No. 37723) and double digested with PvuII and HindIII. The approximately 354 bp PvuII/HindIII fragment containing the rat beta-actin promoter/enhancer was isolated and cloned into the approximately 7005 bp NruI filled/HindIII fragment resulting in plasmid LNBeta-actin-hBMP-7.

Production of Retroviral Vector Particles

The LNCX, LZ12 (Galileo, et al., *Proc. Natl. Acad. Sci. USA* 87, 458–462 (1990)), LNCX-hBMP-7, and LNBeta-actin-hBMP-7 retroviral vector plasmid DNAs were used to generate retroviral vector particles from PA317 cells. PA317 cells were seeded in 8 mls of D10 media in 10 cm dishes at $1 \times 10^6$ cells per dish and transfected the following day with 30 micrograms of LNCX, LZ12, LNCX-hBMP-7, or LNBeta-actin-hBMP-7 plasmid DNA using CaPO4 (5', 3'). The following morning, the media was removed and cells washed with PBS (phosphate buffered saline, pH 7.3, NoCa$^{++}$or Mg$^{++}$) prior to replacement with 8 mls of fresh D10. 24 hours post-wash, transiently produced retroviral vector particles (supernatants) were collected, filtered through 0.22 micron syringe filters (Millipore), and used to transdue primary rabbit periosteal cells. Stable G418 resistant PA317 producer cell populations were also generated and used as a source of retroviral vector particles and filtered and used as described for the transient supernatants.

Analysis of hBMP-7 Expression

CaPO$_4$ transfected PA317-LNCX-hBMP-7 cells died while control CaPO4 transfected PA317-LNCX cells survived upon selection for 10 to 14 days in D10$_{G300}$ (D10 media supplemented with 300 micrograms/ml active Geneticin or G418 (GibcoBRL)). This suggested that the hBMP-7 gene product was toxic to PA317 cells when expressed from a strong promoter/enhancer such as CMV. Therefore, transiently expressed LNCX-hBMP-7 supernatant was used to transduce primary rabbit periosteal cells. After several days selection in G418 (600 micrograms/ml), the periosteal cells became large with a thick coating of material, accompanied by release of the cells from adherence to the tissue culture dish. This material dissolved when the cells were washed with PBS suggesting the material could be hydroxyapatite. Samples of the cells were analyzed and confirmed to contain hydroxyapatite by electron x-ray diffraction.

Subsequently, in the LNBeta-actin-hBMP-7 construct, the hBMP-7 gene was placed under the control of the rat beta-actin promoter/enhancer which is a weaker promoter/enhancer than CMV. CaPO$_4$ tranfected PA317-LNBeta-actin-hBMP-7 producer cells survived when fully selected in D10$_{G600}$ and were used to obtain total RNA using the RNeasy Total RNA kit. Northerns of 5 micrograms of total RNA from LNBeta-actin-hBMP-7 transduced producer cells and periosteal cells were probed with a hBMP-7 specific DNA probe. The LNCX transduced cells showed no bands hybridizing to the probe as expected. However, the LNBeta-actin-hBMP-7 transduced cell lanes showed two bands appearing as expected. The larger more intense band corresponds to the genomic length RNA of approximately 4.7 kb while the less abundant MRNA driven off the beta-actin promoter/enhancer is approximately 2.3 kb.

ELISA data shows protein production from the PA317-LNBeta-actin-hBMP-7 cells secreted into the media. Protein levels of hBMP-7 were analyzed by ELISA using a monoclonal antibody directed against human BMP-5. Human BMP-5, 6 and 7 are 90% identical in amino acid sequence (Wozney, *J. Mol. Repro. Dev.* (1992)) and this antibody is known to be cross-reactive with hBMP-7 by ELISA but not by Western blot. Fully G418 selected populations of PA317 were assayed by ELISA for secreted hBMP-7 in the culture medium. Results clearly show that BMP-7 is detected in the media by cells carrying the LNB-hBMP-7 construct but not by negative control cells carrying only the LNCX construct. This demonstrates that cells genetically modified with BMP-7 are able to produce and secrete BMP-7 into the media while cells not genetically modified with BMP-7 do not secrete detectable levels fo BMP-7.

Transduction of Cells

Primary rabbit periosteal cells were plated into 6 well dishes and cultured in D10 media. Transductions with supernatants were performed by adding 1.6 mls of fresh D10 media supplemented with 8 micrograms/ml polybrene (Sigma) to each well. 400 microliters of supernatant was added to the cells and incubated overnight at 37° C. The following morning, the media was replaced with 2 mls of fresh $D10_{G600}$. As the cells became confluent in the 6 well dishes, they were trypsinized, transferred to 15 cm dishes, and cultured in $D10_{G600}$. When the cells became confluent, they were seeded onto polymer scaffolds for later implantation into rabbit cranial bone defects. The cells expressed BMP-7 mRNA, produced BMP-7 protein and made hydroxyapatite, the essential mineral of bone.

Analysis of Cells and Grafts for Nuclear-betagalactosidase Expression

In a separate study, periosteal cells transfected with lacZ were implanted into rabbit femoral defects.

Cells cultured on plastic, on grafts, or from graft material removed from rabbits after one or two months in vivo were analyzed for nuclear-betagalactosidase expression (Galileo, D. S., Gray, G. E., Owens, G. C., Majors, J., and Sanes, J. R. (1990) *Proc. Natl. Acad. Sci. USA* 87, 458–462). Cells were fixed for 30 minutes in 2% (wt/vol) paraformaldehyde and 0.4% glutaraldehyde in PBS at 4° C. Cells were subsequently washed with PBS and stained for 2 hrs. at 37° C. in a solution of 1 mg/ml X-gal (Molecular Probes), 20 mM potassium ferrocyanide, 20 mM potassium ferricyanide, and 2 mM $MgCl_2$ in PBS.

Modifications and variations of the methods and reagents described herein will be obvious to those skilled in the art. Such modifications and variations are intended to come within the scope of the following claims.

We claim:

1. Isolated mesenchymal cells genetically engineered to express an effective amount of bioactive molecules to enhance the temporal sequence of wound repair, to alter the rate of cell proliferation, to increase the metabolic synthesis of extracellular matrix proteins, and to direct phenotypic expression in endogenous cell populations other than the genetically engineered cells, wherein the bioactive molecules are selected from the group consisting of bone growth factors, cartilage growth factors, nerve growth factors, and general growth factors important in wound healing and tissue repair, wherein the cells are applied to or incorporated into a prosthesis for repair or replacement of bone, cartilage or connective tissue.

2. The cells of claim 1 isolated from periosteal tissue.

3. The cells of claim 1 wherein the bioactive molecules are normally expressed by the cells.

4. The cells of claim 1 wherein the bioactive molecules are selected from the group consisting of bone growth factors, cartilage growth factors, nerve growth factors, and general growth factors important in wound healing.

5. The cells of claim 4 wherein the growth factors are selected from the group consisting of platelet-derived growth factor (PDGF), vascular endothelial growth factor (VEGF), epidermal growth factor (EGF), basic fibroblast growth factor (FGF), insulin-like growth factor (IGF), endothelial derived growth supplement (EDGS), keratinocyte growth factor (KCF), osteogenin, skeletal growth factor (SGF), osteoblast-derived (BDGFs), retinoids, growth hormone (GH), bone morphogenic proteins (BMPs), and transferrin.

6. The cells of claim 4 wherein the bioactive molecules are selected from the group of TGF-beta superfamily proteins consisting of bone morphogenic proteins (BMP), TGF-beta, and insulin-like growth factor (IGF).

7. The cells of claim 1 wherein the prosthesis is formed of a biocompatible polymer.

8. Isolated cells genetically engineered to express an effective amount of bioactive molecules to enhance the temporal sequence of wound repair, to alter the rate of cell proliferation, to increase the metabolic synthesis of extracellular matrix proteins, and to direct phenotypic expression in endogenous cell populations other than the genetically engineered cells, wherein the cells are selected from the group consisting of nerve cells, epidermal cells, dermal cells, and periosteal cells, and the bioactive molecules are selected from the group consisting of bone growth factors, cartilage growth factors, nerve growth factors, and general growth factors important in wound healing and tissue repair, and wherein the cells are applied to or incorporated into a prosthesis for repair or replacement of bone, cartilage or connective tissue.

9. The cells of claim 8 wherein the cells are periosteal cells genetically engineered to express BMP-7.

* * * * *